United States Patent [19]

Falk et al.

[11] Patent Number: 4,569,641

[45] Date of Patent: Feb. 11, 1986

[54] LOW POWER ELECTROMAGNETIC PUMP

[75] Inventors: Theodore J. Falk, Clarence; Lawrence E. Morris, Bowmansville, both of N.Y.

[73] Assignee: Greatbatch Enterprises, Inc., Clarence, N.Y.

[21] Appl. No.: 415,657

[22] Filed: Sep. 7, 1982

[51] Int. Cl.[4] .................. F04B 17/04; F04B 7/00; H02K 33/02

[52] U.S. Cl. .................. 417/417; 417/444; 417/505; 417/DIG. 1; 310/30; 310/89; 310/104

[58] Field of Search ............... 417/417, 416, 240, 241, 417/505, 487, 444, 445, DIG. 1; 310/32, 30, 28, 89, 104

[56] References Cited

U.S. PATENT DOCUMENTS

| 1,590,868 | 6/1926 | Wallace | 417/417 |
|---|---|---|---|
| 2,568,757 | 9/1951 | Mesh | 310/30 |
| 2,634,805 | 4/1953 | Bills et al. | 417/417 X |
| 2,951,447 | 9/1960 | Casassa | 310/104 X |
| 3,601,509 | 8/1971 | Kreitchman | 417/417 |
| 4,043,706 | 8/1977 | Walker | 310/104 X |
| 4,244,229 | 1/1981 | Pullen | 73/708 X |

FOREIGN PATENT DOCUMENTS

55-84880  6/1980  Japan .......................... 417/DIG. 1

Primary Examiner—Cornelius J. Husar
Assistant Examiner—Peter M. Cuomo
Attorney, Agent, or Firm—Christel, Bean & Linihan

[57] ABSTRACT

An electromagnetic pump comprising a housing having fluid receiving and pumping chambers in communication with an inlet and an outlet, respectively, an electromagnet carried by the housing external to the fluid chambers, and a barrier in the form of a thin diaphragm of fluid impermeable material which hermetically isolates the electromagnet from the fluid chamber. An armature in the housing is movable within a body of magnetically permeable material and has a pole portion located for magnetic attraction by the electromagnet and has a plunger portion in the pumping chamber for forcing fluid out of the chamber through the outlet. The armature is moved from a rest position through a forward pumping stroke when attracted by the electromagnet to force fluid out of the pumping chamber through the outlet, and the armature is moved by biasing spring in an opposite direction through a return stroke back to the rest position. The pump is made electrically and magnetically efficient by minimizing the total gap within the magnetic circuit, by having the pole face area relatively large on the armature pole portion, and by having the electromagnet include a coil or a core of relatively small diameter. A pump check valve closes the pump inlet when the armature is in the rest position and opens the inlet after the armature begins the forward pumping stroke.

42 Claims, 18 Drawing Figures

LOW POWER ELECTROMAGNETIC PUMP

BACKGROUND OF THE INVENTION

This invention relates to the art of electromagnetically-operated fluid pumps, and more particularly to a new and improved electromagnetic pump which operates at extremely low power.

One area of use of the present invention is implantable drug delivery systems, although the principles of the present invention can be variously applied. The principal requirements for a pump in such applications are low power drain, since the pump must be driven by an implanted battery, and compatibility with the drug being pumped. It would, therefore, be highly desirable to provide an electromagnetically-operated pump which is safe, reliable, small in size, light in weight, which operates without excessive demand on the available energy supply and which is compatible with drugs or similar liquids to be pumped.

SUMMARY OF THE INVENTION

It is, therefore, a primary object of this invention to provide a new and improved electromagnetically-operated pump.

It is a more particular object of this invention to provide such a pump which operates at extremely low power levels.

It is a further object of this invention to provide such a pump which is compatible with drugs and similar liquids to be pumped.

It is a more particular object of this invention to provide such a pump which is small in size, light in weight and reliable in operation.

It is a further object of this invention to provide such a pump which is electrically and magnetically efficient.

The present invention provides an electromagnetic pump comprising a housing having fluid receiving and pumping chambers therein and in communication with an inlet and an outlet, respectively, electromagnet means carried by the housing located external to the fluid chambers thereof, and barrier means in the form of a thin diaphragm of fluid impermeable material which hermetically isolates the electromagnet from the fluid chamber. An armature in the housing is movable within a body of magnetically permeable material and has a pole portion located for magnetic attraction by the electromagnet and has a plunger portion in the pumping chamber for forcing fluid out of the chamber through the outlet. The armature is moved from a rest position through a forward pumping stroke when attracted by the electromagnet means to force fluid out of the pumping chamber through the outlet, and the armature is moved by biasing means in an opposite direction through a return stroke back to the rest position. A magnetic circuit is defined including the electromagnet means, a portion of the fluid-impermeable barrier, the body, the armature pole portion and a gap defined between the pole portion and the electromagnet which gap is closed during movement of the armature toward the electromagnet during energization thereof. The pump is made electrically and magnetically efficient by minimizing the total gap within the magnetic circuit, by having the pole face area relatively large on the armature pole portion, and by having the electromagnet include a coil or a core of relatively small diameter. A pump check valve can be provided separately or incorporated integrally with the armature in the form of a valve member movably carried by the armature and positioned for closing the pump inlet when the armature is in the rest position and opening the inlet after the armature begins the forward pumping stroke.

The foregoing and additional advantages and characterizing features of the present invention will become clearly apparent upon a reading of the ensuing detailed description together with the included drawing wherein:

DETAILED DESCRIPTION OF THE ILLUSTRATED EMBODIMENTS

Figures 1, 2, 3:
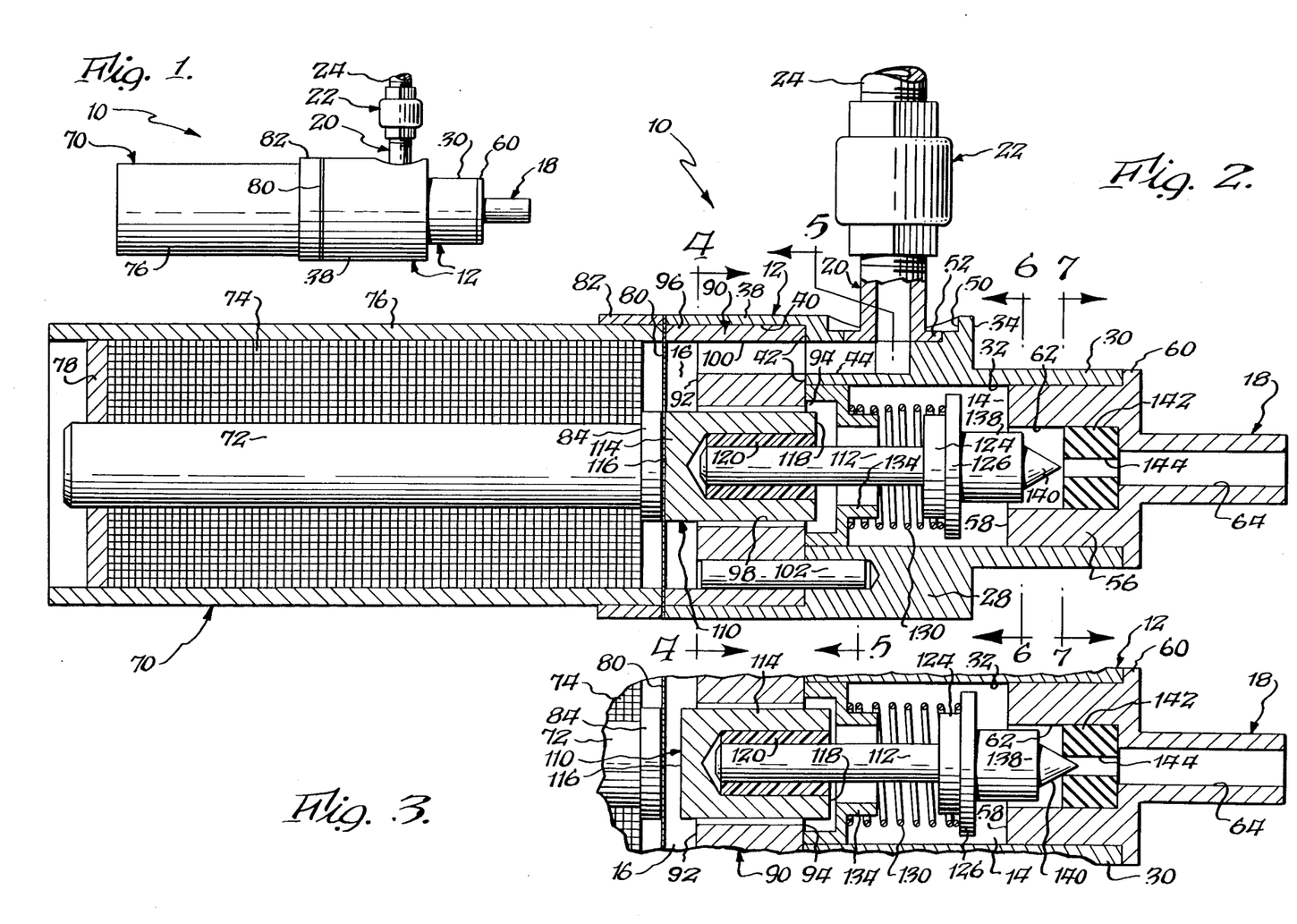
FIG. 1 is a side elevational view of a pump according to one embodiment of the present invention.
FIG. 2 is an enlarged longitudinal sectional view, partly in elevation, of the pump of FIG. 1.
FIG. 3 is a fragmentary longitudinal view of the pump of FIG. 2 showing the armature in a rest position.
Figure 4:
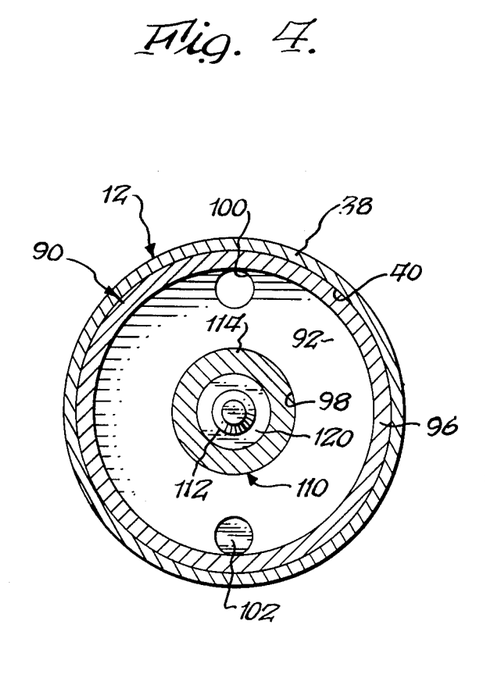
FIG. 4 is a sectional view taken about on line 4—4 in FIG. 2.
Figure 5:
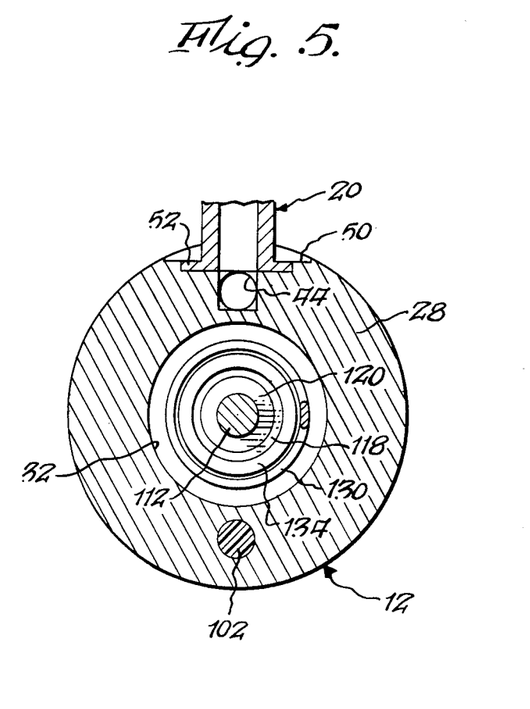
FIG. 5 is a sectional view taken about on line 5—5 in FIG. 2.
Figure 6:
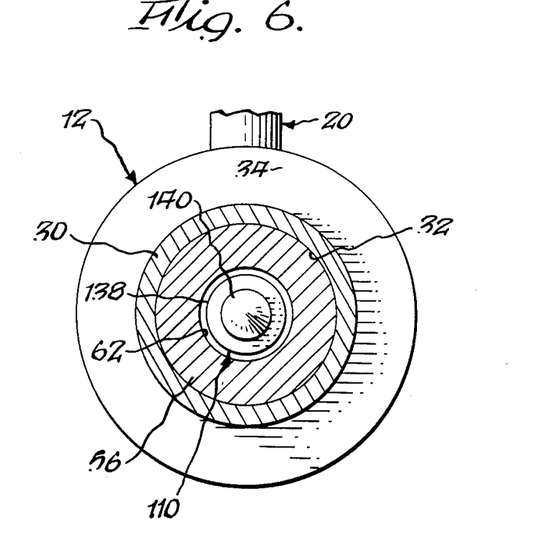
FIG. 6 is a sectional view taken about on line 6—6 in FIG. 2.
Figure 7:
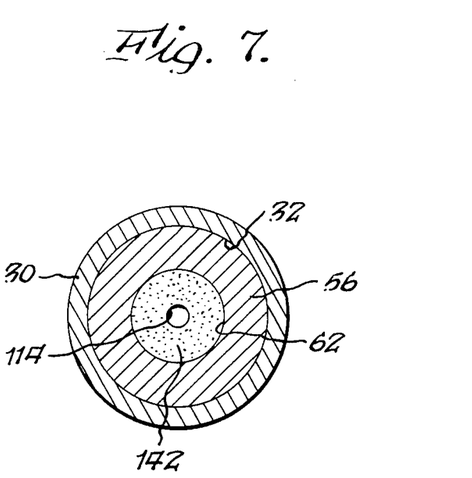
FIG. 7 is a sectional view taken about on line 7—7 in FIG. 2.

Referring now to FIGS. 1-7, a pump 10 according to one embodiment of the present invention includes a housing 12 which is generally hollow cylindrical in overall shape and includes an interior region for containing fluid, i.e. the liquid to be pumped. As shown in FIG. 2, the hollow interior region is divided in a manner which will be described into a fluid receiving chamber 14 and a fluid pumping chamber 16 in fluid communication therewith. There is an inlet generally designated 18 in fluid communication with the receiving chamber 14 and adapted to be connected to a source or supply of fluid to be pumped. There is also an outlet 20 in fluid communication with the pumping chamber 16 and adapted to be in fluid communication with a location to which the fluid is to be pumped.

There is provided check valve means operatively associated with the fluid containing region of pump 10 for allowing fluid flow in a direction from the inlet 18 through outlet 20 and blocking fluid flow in a direction from the outlet through the inlet. In the pump of this embodiment a check valve 22 is connected between outlet 20 and a conduit 24 for supplying pumped fluid to a location of use.

Referring now to FIG. 2, housing 12 is generally hollow cylindrical in overall shape including a central body portion 28 of relatively substantial wall thickness. Housing 12 also includes a first axial end portion 30 extending from one end of body portion 28, i.e. the right-hand end as viewed in FIG. 2, and which is of relatively smaller wall thickness. Portions 28 and 30 define the interior region of constant diameter having an inner surface 32. Thus, the outer surfaces of portions 28 and 30 are of different diameters and meet in an annular surface 34. The housing 12 has a second axial end portion 38 extending from the other end of body 28, i.e. the left-hand end as viewed in FIG. 2, which also is of smaller wall thickness. End portion 38 has a relatively larger diameter inner wall surface 40 which meets surface 32 in annular intermediate wall 42.

Body portion 28 is provided with a longitudinal bore or passage 44 for placing pumping chamber 16 in fluid communication with outlet 20. Outlet 20 is located on the side of housing 12 for communication with the passage 44. Housing portion 28 is provided with a radially inwardly extending opening in the outer wall thereof in communication with passage 44. The opening is formed to include an annular recess 50 defining a ledge which engages an annular rim 52 of a tubular fitting which defines the outlet 20.

Inlet 18 is provided by a plug-like element which is fitted into the open end of the housing axial end portion 30. The element includes a main body 56 generally cylindrical in shape and having an outer diameter substantially equal to the diameter of inner wall surface 32 thereby providing a close fit therein. Body 56 has one axial end face 58 located in chamber 14, and adjacent the opposite end the outer surface of body 56 is provided with an annular rim 60 which abuts the annular end face of housing portion 30 for placement and securement of the fitting in the housing. The two components are secured together by welding or other suitable means. The body portion 56 has an internal wall surface 62 defining a region of substantial diameter. The inlet portion 18 is defined by a relatively smaller diameter portion of the plug element having an internal passage 64 of relatively smaller diameter compared to passage 62. Inlet 18 is adapted for connection to a conduit such as a flexible tubing leading from a source or supply of fluid to be pumped.

By way of example, in an illustrative pump, housing 12 and the inlet and outlet fittings 18 and 20, respectively, all are of metal, and for a drug delivery pump for implantation in a patient, titanium has been found to provide satisfactory results. In such an illustrative pump, housing 12 has an overall length of about 0.425 inch measured between the axial end faces of portions 30 and 38. Surface 32 has a diameter of about 0.15 inch, and the axial end face of portion 30 has a radial dimension of about 0.03 inch. Surface 40 has a diameter of about 0.26 inch, and the axial end face of housing portion 38 has a radial thickness of about 0.02 inch. Passage 44 in housing body 28 and the interior passage in outlet fitting 20 both have a diameter of about 0.032 inch. In the inlet plug fitting 18, the passage 62 has a diameter of about 0.073 inch and passage 64 has a diameter of about 0.032 inch.

The pump of the present invention further comprises electromagnet means generally designated 70 carried by housing 12 and located external to the fluid containing region of the housing. As shown in FIG. 2, the electromagnet 70 includes a core 72 in the form of a spool which is generally solid cylindrical in shape. A coil 74 is wound on spool 72 and contained within a hollow housing 76 generally cylindrical in shape. One end of electromagnet 70 is adjacent and in abutting relation to housing 12, and the opposite end, i.e. the left-hand end as viewed in FIG. 2, is closed by a plate element 78 fitted within the open end of housing 76 and fitted onto an end of spool 72. Electromagnet 70 is joined to housing 12 in the following manner.

The interior, fluid containing region of housing 12 and the electromagnet 70 are separated by a barrier means of fluid impervious material in the form of a relatively thin plate or diaphragm-like component 80. The end of magnet housing 76 adjacent housing 12 is provided with an annular band 82 around the outer surface and adjacent the axial end face of housing 76. The outer diameter of band 82 when placed on housing 76 is substantially equal to the outer diameter of housing portion 38 so that the respective outer surfaces are substantially flush. The axial end faces of band 82 and magnet housing 76 are coplanar. The housing and electromagnet structures are placed in abutting relation on opposite surface portions of the plate 80, and the assembly secured together by a weld joining the respective adjacent outer surfaces of band 82 and housing portion 38. In addition, an enlarged annular end portion 84 of spool 72 contacts the central portion of plate 80 in a manner supporting the same.

By way of example, in an illustrative pump, spool 72, magnet housing 76 and closure 78 are of ferromagnetic material, for example 0.4750 nickel iron alloy. Plate 80 and band 82 are of titanium, the material of plate 80 being found suitable for use in the exemplary implanted drug deliver pump previously mentioned. Spool 72 has a length of about 0.555 inch and a diameter of 0.079 inch. Housing 76 has a wall thickness of about 0.03 inch, band 82 a thickness of about 0.02 inch and diaphragm 80 a thickness of about 0.001 inch. Coil 74 has about 3600 turns of 42 gauge wire.

The pump of the present invention further comprises a body 90 of magnetically permeable material in the fluid containing region of housing 12 and between the fluid receiving chamber 14 and the fluid pumping chamber 16. In addition to providing separation between the two chambers, body 90 also defines a portion of the magnetic circuit in the pump, along with other components of the pump, in a manner which will be described. Body 90 is generally solid cylindrical in shape having an outer diameter substantially equal to the diameter of housing inner surface 40 thereby providing a close fitting relationship. Body 90 has a main body portion between axial end surfaces 92 an 94 which is of an axial length less than the distance between housing surface 42 and plate 80 by an amount determined by the desired dimension of pumping chamber 16. Body 90 is formed to include an outer annular rim portion 96 extending from end face 92 and which abuts a corresponding surface portion of plate 80 as shown in FIG. 2. The radial thickness of rim portion 96 is substantially equal to that of magnet housing 76, and the two are in substantial alignment for maximizing transmission of magnetic flux therebetween in a manner which will be described. Body 90 is provided with a central through bore or passage 98 of substantial diameter for receiving a portion of the pump armature in a manner which will be described. The main portion of body 90 also is provided with a smaller through bore or passage 100 offset from passage 98 and of substantially the same diameter and in registry with outlet passage 44 thereby providing fluid communication between pumping chamber 16 and the outlet 20. Body 90 is positioned in housing 12 by means of a rod 102 extending through corresponding bores in body 90 and valve housing portion 28 shown in FIG. 2, the rod 102 preferably being of Teflon material and the parts being secured together by a compression fit.

By way of example, in an illustrative pump, body 90 is of mu metal which is selected to provide the desired degree of magnetic permeability while at the same time being compatible with medicine or the like for use in the exemplary implanted drug delivery pump previously mentioned. As is well known, mu metal includes nickel in a major portion with the balance including iron, copper and chromium. In addition, some or all of the external surfaces of body 90 can be plated or coated with gold or other suitable material chose to enhance the compatibility of the drug with the external surface. The outer diameter of body 90 is about 0.26 inch, the axial length between end face 94 and the end face or rim 96 is about 0.130 inch, and the axial length between end faces 92,94 is about 0.1 inch. Passage 100 has a diameter of about 0.029 inch and the central passage 98 a diameter of about 0.1 inch.

The pump according to the present invention further comprises an armature generally designated 110 positioned in the fluid containing region of housing 12. The armature has a pole portion located for magnetic attraction by the electromagnet 70 and has a plunger portion in the pumping chamber 16 for forcing fluid out of the chamber and outlet 20. The armature 110 is movably supported in housing 12 for movement from a rest position through a forward pumping stroke when attracted by the electromagnet 70 to force fluid out of the pumping chamber 16 through outlet 20, and for movement in an opposite direction through a return stroke back to the rest position. In FIG. 2, armature 110 is shown in a position at the end of the forward pumping stroke in response to energization of electromagnet 70, and in FIG. 3 armature 110 is shown in the rest position at the end of the return stroke which will be described in detail presently.

Armature 110 includes a shaft or rod portion 112 which is positioned in housing 12 with the longitudinal axis thereof generally coincident with the longitudinal axis of housing 12. A major portion of the length is a section of relatively small diameter. The armature further includes an enlarged body portion 114 of magnetically permeable material which provides the armature pole portion and the plunger portion in a manner which will be described. Body 114 is solid cylindrical in shape having an outer diameter slightly smaller than the diameter of passage 98 in body 90. This is to allow reciprocal movement of armature body 114 within the body 90 during the forward and return strokes of armature 110. In addition, the sizes of the outer diameter of body 114 and the diameter of passage 98 are selected to provide a fluid leakage path from pumping chamber 16 to receiving chamber 14 during the armature return stroke in a manner which will be described. The armature body 114 terminates at the end facing electromagnet 70 in an axial end face 116 which serves as the pole face and is disposed substantially perpendicular to the armature axis. The pole face 116 together with electromagnet 70 define the magnetic circuit gap which is closed during the forward pumping stroke. The pole face 116 is of relatively large cross-sectional area as compared to the cross sectional area of the armature shaft portion 112. The body 114 also serves as the plunger portion of the armature because as the pole face 116 moves toward plate 80 during the forward stroke when magnet 70 is energized, body 114, upon moving into pumping chamber 116, displaces fluid therefrom forcing it out through passages 100,44 to outlet 20.

Shaft portion 112 is fixed to body 114 in the following manner. Body 114 is provided with a longitudinal bore extending inwardly from the opposite axial end face 118 which terminates within body 114 at a location spaced from pole face 116. A sleeve 120 of fluoropolymer material such as Teflon is fitted in the bore, and the end of the armature shaft portion 112 is fixed in the sleeve or bushing 120. The foregoing is provided by a mechanical compression fit.

Armature 110 includes two relatively larger diameter shaft sections spaced axially from body 114 in a direction opposite therefrom. In particular, there is a first section 124 facing body 114 and a second, axially adjacent section 126 which of slightly larger diameter. The two sections 124,126 are of relatively short axial length, and they define therebetween an annular shoulder facing the body 114.

There is also provided biasing means in the form of a coil spring 130 for urging armature 110 toward the rest position shown in FIG. 3. One end of spring 130 seats in the annular shoulder defined by the armature shaft sections 124,126. The opposite end of spring 130 seats in an annular spring retainer element 134 which has an annular rim portion which abuts against the end face 94 of body 90 as shown in FIG. 2. The annular shape of retainer 134, with the two diameter rim sections, enables it to be located concentric with the armature shaft section 112 to receive the spring 130 which also is concentric with the shaft, while at the same time not interfering with body 114 during movement of the armature 110. The outer diameter of the largest rim portion of retainer 134 is substantially equal to the diameter of surface 32, and retainer 134 is merely located within the housing 12, being held in place by the force of spring 130.

Armature 110 has a valve portion at the axial end of the armature opposite that of the pole face 116 for closing the inlet 18 when the armature is in the rest position and for opening inlet 18 when the armature is moved during the forward pumping stroke. There is provided an armature shaft section 138 having an outer diameter slightly less than the diameter of passage 62 in body 56. Section 138 terminates in a conical tip formation 140 at the axial end of the armature. The tip 140 is adapted for movement into and out of seating engagement with a body 142 fitted in passage 62 and having a longitudinal passage 144 therein in communication with inlet passage 64. In particular, the surface of cone 140 contacts the edge of opening 114 during seating of the valve to block fluid communication between inlet 18 and receiving chamber 14. In the device shown, passage 114 is of smaller diameter than passage 64. The tip 140 is of metal and the element 142 is of relatively soft material, for example silicone rubber, to facilitate the seating of element 140 therein.

By way of example, in an illustrative pump, the armature rod or shaft portion including the sections 112, 124, 126, 138 and 140 is machined from metal, preferably titanium for use in the aforementioned illustrative implanted drug delivery pump. Armature body 114 is of mu-metal, retainer 134 is of titanium and body 142 can be cut from a length of silicone rubber tubing. In addition, armature body can be coated or plated with gold, or other suitable material, like body 90, chosen to enhance the compatibility of the drug with the external surface. Also, the outer surface of body 114 received in passage 98 can be coated with Teflon to reduce friction. The armature shaft or rod portion has an overall length of about 0.34 inch from the end fitted within body 114 to the end of the conical tip 140. The smaller diameter section 112 of major axial length has a diameter of about 0.036 inch, and the relatively larger diameter sections 124 and 126 have diameters of about 0.093 and 0.136 inch, respectively, and axial lengths of about 0.035 and 0.015 inch, respectively. Section 138 has a diameter of about 0.068 inch and a length of about 0.058 inch, and conical tip 140 has an axial length of about 0.037 inch and a base angle of about 60°. Body 114 has an overall axial length of about 0.14 inch and an outer diameter of about 0.1 inch. Spring 130 is 0.006 titanium wire and the passage 144 in body 142 has a diameter of about 0.015 inch.

In operation, inlet 18 is connected to a source or supply of fluid to be pumped, and conduit 24 leading from check valve 22 is connected to a point or location of use for the pumped fluid. The armature 110 is moved through the forward pumping stroke in response to electrical energization of electromagnet 70. One way of energizing magnet 70 is to charge a capacitor from a battery and then discharge that capacitor through coil 74. Other procedures can of course be employed for electrically energizing coil 74 in a known manner. Prior to electrical energization of magnet 70, armature 110 is in the rest position illustrated in FIG. 3 where the valve at the end of armature 110 in the form of conical tip 140 is seated in opening 144 to block fluid communication from inlet 18 to the fluid receiving chamber 14. In the rest position of armature 110, pole face 116 is spaced from diaphragm 80 as shown in FIG. 3 thereby defining the gap in the magnetic circuit. In the rest position this gap between pole face 116 and diaphragm 80 is of maximum length.

When coil 74 is electrically energized, the armature pole portion 114 is attracted toward magnet 70 thereby causing armature 110 to be drawn toward diaphragm 80. Electromagnetic flux travels through the magnetic circuit including the electromagnet core 72, plate 78, magnet housing 76, rim 96 of body 90, the included portion of diaphragm 80 between housing 76 and rim 96, body 90, armature pole portion 114, and the gap between pole face 116 and diaphragm 80. As armature 110 is moved in the forward pumping stroke, i.e. in a direction to the left as viewed in FIGS. 2 and 3, fluid initially contained in the pumping chamber 16, i.e. the region between body 90, diaphragm 80 and pole portion 114, is thereby forced through passages 100 and 44 out through the outlet 20 and through check valve 22 to the conduit 24. The clearance between armature pole portion 114 and the passage 98 in the body 90 is selected to be sufficiently small so that fluid leakage therebetween is relatively small during the forward pumping stroke of armature 110. During the forward pumping stroke, the armature valve portion 140 becomes unseated from the opening of passage 144 thereby allowing fluid flow from inlet 18 into receiving chamber 14 thereby filling the same. The forward pumping stroke of armature 110 is completed when pole face 116 approaches contact with diaphragm 80. Actual contact may not be achieved since viscosity limits outflow of the fluid between the pole face 116 and diaphragm 80.

When electrical excitation of coil 74 ceases, armature 110 is moved in the opposite direction, i.e. to the right as viewed in FIGS. 2 and 3, by the force of biasing spring 130 until the armature reaches the rest position as shown in FIG. 3 with conical tip 140 seated in the opening of passage 144. This motion is relatively slow since it is limited by the small leak rate of fluid between the outer surface of pole portion 114 and the surface of passage 98 in body 90 at a pressure difference determined by the force applied by the spring 130. Thus fluid leakage fills chamber 16 from chamber 14. Thus, the average pumping rate which is determined by the rate of return of armature 110 to the rest position can be relatively slow, but such a pumping rate is called for in typical implantable drug delivery systems. Armature 110 then remains in the rest position of FIG. 3 closing inlet 18 and waiting for the next forward pumping stroke which occurs when magnet 70 is energized again.

The non-movable diaphragm 80 of titanium or like material provides an hermetic seal between the fluid in housing 12 and the electrical components associated with magnet 70. Having armature 110 immersed in the fluid makes operation of the pump nearly independent of ambient pressure. The initial condition of the pump when armature 110 is in the rest position of FIG. 3 is that the fluid is at substantially the same pressure on opposite sides of the pole portion 114, i.e. in the receiving chamber 14 and in the pumping chamber 16.

The pump of the present invention is made electrically and magnetically efficient by minimizing the total gap within the magnetic circuit, by having the magnetic pole face 116 of relatively large surface area, and by having core 72 of relatively small diameter. In particular, there is a relatively large contact area at the interface between the axial end face of magnet housing 76 and diaphragm 80 and between diaphragm 80 and the axial end face of rim 96 of body 90 to minimize the effective air gap introduced by diaphragm 80 at this point in the magnetic circuit. Related to this is the need for welding diaphragm 80 to the band 82 and housing part 38 to achieve an hermetic seal between electromagnet 70 and the fluid containing region of housing 12 while at the same time not adversely affecting the magnetic circuit. In addition, there is a relatively large surface area along the gap between body 90 and pole portion 114 to minimize the effective air gap introduced at this point in the magnetic circuit. The relatively small diameter of core 72 provides the necessary ampere turns with a minimum electrical resistance. The large area of pole face 116 provides a high magnetic force with a minimum number of ampere turns. Having the magnetic gap external to coil 74, i.e. between pole face 116 and diaphragm 80, allows the foregoing features to be achieved simultaneously. The external Teflon coating over the gold plating on pole portion 114 reduces magnetic side loading on armature pole portion 114 and reduces operating friction. The combination of the conical formation 140 and the relatively soft body 142 enables the armature 110 to be self-aligning and permits relatively loose tolerance in construction. The pump of the present invention is relatively small in size having an overall diameter of around 7 millimeters and an overall length of about 27 millimeters, and has the relatively light weight of about 4.5 grams.

FIGS. 8-14 show a pump according to another embodiment of the present invention. In this embodiment, the pump includes a check valve which is integral with the armature, i.e. the check valve is operatively coupled to the armature and is located in the fluid-receiving region of the housing for opening and closing the pump inlet. In particular, in this embodiment of the present invention the check valve comprises a valve member movably carried by the armature and positioned for closing the pump inlet when the armature is in the rest position and for opening the inlet after the armature begins movement associated with the forward pumping stroke. For convenience in illustration, components of the pump of this embodiment which are similar to those of the pump of FIGS. 1-7 are identified by the same reference numerals provided with a prime designation.

Figures 8, 9:
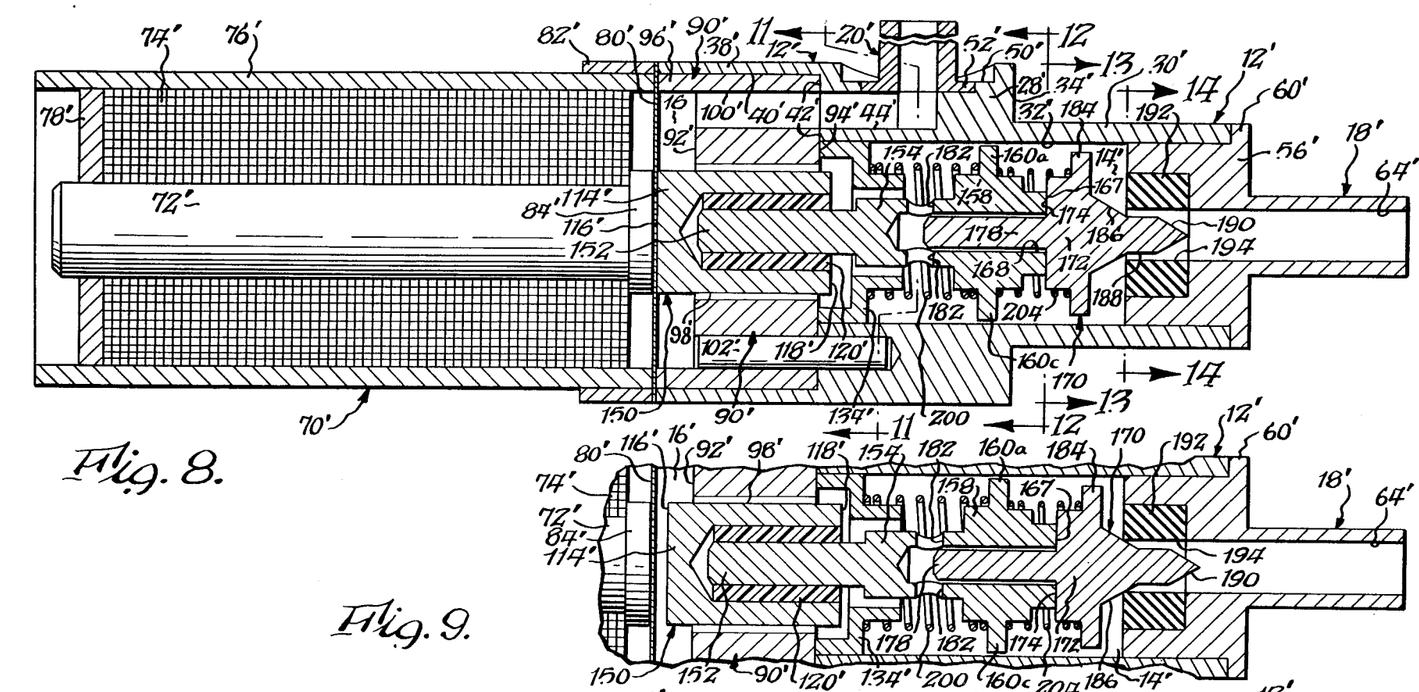
FIG. 8 is a longitudinal sectional view of a pump according to another embodiment of the present invention.
FIG. 9 is a fragmentary longitudinal sectional view of the pump of FIG. 8 showing the armature in a rest position.
Figure 12:
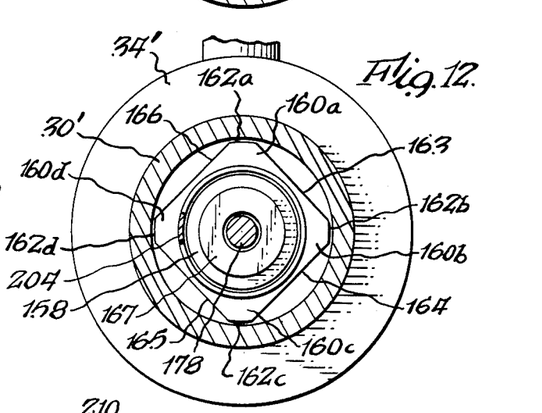
FIG. 12 is a sectional view taken about on line 12—12 in FIG. 8.
Figure 13:
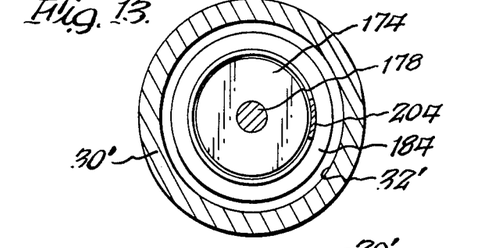
FIG. 13 is a sectional view taken about on line 13—13 in FIG. 8.
Figure 14:
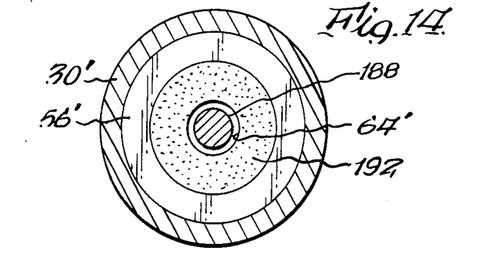
FIG. 14 is a sectional view taken about on line 14—14 in FIG. 8.

The pump of this embodiment has an armature generally designated 150 including a shaft section 152 of relatively small diameter adajcent one end of the armature, i.e. the left-hand end as viewed in FIG. 8. Shaft section 152 is similar to seciton 112 in the embodiment of FIGS. 1-7 but is of relatively shorter axial length. An armature pole portion 114' having a pole face 116' and identical to the pole portion and pole face of the armature of FIGS. 1-7 is fixed to this end of shaft section 152 by a compression fit between pole portion 114', a Teflon bushing 120' and the shaft section in a manner identical to that of the preceeding embodiment. Armature 150 includes a shaft section 154 of slightly larger diameter adjacent shaft section 152 in a direction away from end face 118' of pole portion 114'. Section 154, in turn, meets an armature body portion 158 of larger diameter and formed to include a plurality, in the present illustration four, radially extending formations or lands 160a-160d as shown also in FIG. 12. Each land formation 160a-160d has a relatively short, curved outer edge 162a-162d, respectively, close to the inner surface 32' for guiding the armature 150 as it moves within the housing. Each land is separated from an adjacent land by a corresponding straight edge 163, 164, 165 and 166 as shown in FIG. 12 thereby providing a flow space of significant area between the particular straight edge and the corresponding curved portion of surface 32'. The lands 160a-160d also define a plurality of shoulders facing in opposite axial directions for a purpose to be described. Armature 150 terminates in an axial end face 167 disposed toward inlet 18'. A longitudinal bore 168 extends inwardly from face 167 along within body 158 and terminates in the shaft section 154 for movably carrying the check valve member 170 which now will be described.

Check valve 170 has a main body 172 and an axial face 174, and the check valve 170 is positioned with face 174 disposed toward the armature end face 167. Check valve 170 has a rod or shaft portion 178 extending outwardly in a direction normal to end face 174 and is received in armature passage 168 in slidably movable relation. The armature shaft portion 154 is provided with a pair of oppositely directed radially extending bores or passages 182 in communication with the longitudinal passage 168 at the end where check valve shaft portion 178 terminates for a purpose to be described.

The check valve body 172 has a relatively large diameter portion 184 of relatively short axial length defining an annular shoulder facing toward the lands 160a-160d of the armature. The opposite axial end of valve member 170 includes a frustoconical surface 186, a cylindrical surface 188 and a conical tip formation 190. These portions of valve 170 extend into an annular valve seat element 192 having a central bore or passage 194, which, in turn, is fixed in the annular recess of body 56' of the fitting defining inlet 18'.

There is also provided first biasing means in the form of coil spring 200 between a spring retainer 134' and the annular shoulders defined by lands 160a-160d for urging armature 150 into the rest position. There is also provided second biasing means in the form of coil spring 204 positioned between the annular shoulder defined by lands 160a-160d and the annular shoulder defined by valve section 184 for urging check valve 170 into the position closing inlet 18'.

By way of example, in an illustrative pump, the components identified by the primed reference numerals are of the same material and of substantially the same dimensions as corresponding components in the embodiment of FIGS. 1-7. With respect to armature 160, pole portion 114' is of the same material and of substantially the same size as pole portion 114 in FIGS. 1-7. The remainder of the armature 150 is of titanium, and the overall length measured between the left-hand and of shaft portion 152 as viewed in FIG. 8 to axial end face 167 is about 0.285 inch. Shaft section 152 has a length of about 0.130 inch and a diameter of about 0.036 inch. Shaft section 154 has a length of about 0.080 inch and a diameter of about 0.055 inch. Body 158 has a length of about 0.075 inch and a diameter of about 0.093 inch. Each of the land portions 160a-160d has an axial length of about 0.040 inch, each edge 162a-162d has a length of about 0.020 inch, and edges 162a-162d lie about on a circle having a diameter of about 0.146 inch.

Valve member 170 is of titanium, and has an overall length of about 0.215 inch between the outer end face of shaft portion 178 to the top of core 190. Shaft portion 178 has a length of about 0.100 inch and a diameter of about 0.025 inch. The two sections of body 172 have outer diameters of 0.093 inch and 0.136 inch. Surface 186 has a base angle of about 60° and an axial length of about 0.03 inch. The combined axial lengths of surfaces 188 and 190 is about 0.050 inch, surface 188 has a diameter of about 0.030 inch and surface 190 has a base angle of about 60°. Valve seat member 192 is of silicone rubber tubing having an outer diameter of about 0.100 inch and an inner diameter of about 0.040 inch. Spring 200 provides a force of about 3.5 grams and spring 204 a force of about 1.5 grams.

In operation, inlet 18' is connected to a source or supply of fluid to be pumped, and outlet 20' is connected to a point or location of use for the pumped fluid. The armature 150 is moved through the forward pumping stroke in response to electrical energization of electromagnet 70'. As in the proceeding embodiment, one way of energizing magnet 70' is to charge a capacitor from a battery and then discharge that capacitor through coil 74. Other procedures can of course be employed for electrically energizing coil 74' in a known manner. Prior to electrical energization of magnet 70', armature 150 is in the rest position illustrated in FIG. 9 where the check valve 170 is located with frustoconical surface 186 seated in the opening of passage 194 to block fluid communication from inlet 18' to the fluid receiving chamber 14'. In the rest position of armature 150, pole face 116' is spaced from diaphragm 80' as shown in FIG. 9 thereby defining the gap in the magnetic circuit. In the rest position this gap between pole face 116' and diaphragm 80' is of maximum length.

When coil 74' is electrically energized, the armature pole portion 114' is attracted toward magnet 70' thereby causing armature 150 to be drawn toward diaphragm 80. Electromagnetic flux travels through the magnetic circuit including the electromagnet core 72', plate 78', magnet housing 76', rim 96' of body 90', the included portion of diaphragm 80 between housing 76' and rim 96', body 90', armature pole portion 114', and the gap between pole face 116' and diaphragm 80'. As armature 150 is moved in the forward pumping stroke, i.e. in a direction to the left as viewed in FIGS. 8–10, fluid initially contained in the pumping chamber 16', i.e. the region between body 90', diaphragm 80' and pole portion 114' is thereby forced through passages 100' and 44' and out through the outlet 20'. The clearance between armature pole portion 114' and the passage 98' in body 90' is selected to be sufficiently small so that fluid leakage therebetween is relatively small during the forward pumping stroke of armature 150.

The check valve member 170 slides freely with respect to the armature 150 and does not necessarily move when the armature 150 is drawn toward diaphragm 80'. Such relative positions are illustrated, for example, in FIG. 10. At rest, the surface 186 of valve member 170 is held in contact with the valve seat defined by passage 194 by the spring 200 acting upon the armature 150 which is then in contact with the check valve member 170 as shown in FIG. 9. When the armature 150 is drawn toward diaphragm 80' the force of spring 200 is no longer transferred to the check valve member 170 and the force holding the valve member 170 against the valve seat is decreased to that provided by spring 204, which generally provides a force less than that provided by spring 200. If armature 150 is drawn toward electromagnet 70' with sufficient velocity, pressure within the pump housing 12' between body 90' and the check valve seat decreases to a level below the level at the pump inlet 18' and the net force due to fluid pressure from inlet 18' acting on the check valve member 170 tends to move the valve member 170 away from its seat. If the net force due to the fluid pressure exceeds that applied by the spring 200, then valve member 170 moves away from the valve seat and fluid flows into the pump body as illustrated in FIG. 8. In fact, because the fluid is nearly incompressible the check valve 170 opens at approximately the same time that the armature 150 achieves enough velocity to force fluid out of the pump outlet 20'. The forward pumping stroke of the armature 150 is completed when the pole face 116' approaches contact with the diaphragm 80'. Actual contact may not be achieved since viscosity limits outflow of the fluid between the pole face 116' and the diaphragm 80'. When the armature velocity decreases to a level such that the displacement rate of the motion of the pole portion 114' no longer exceeds the leak rate between the pole portion 114' and the body 90', the pressure within the pump housing 12' begins to increase. When the force due to the pressure difference across the check valve member 170 no longer exceeds the force of spring 204, the check valve member moves toward the valve seat and prevents flow out of the inlet port 18' of the pump as illustrated, for example, in FIG. 10.

Figure 10:
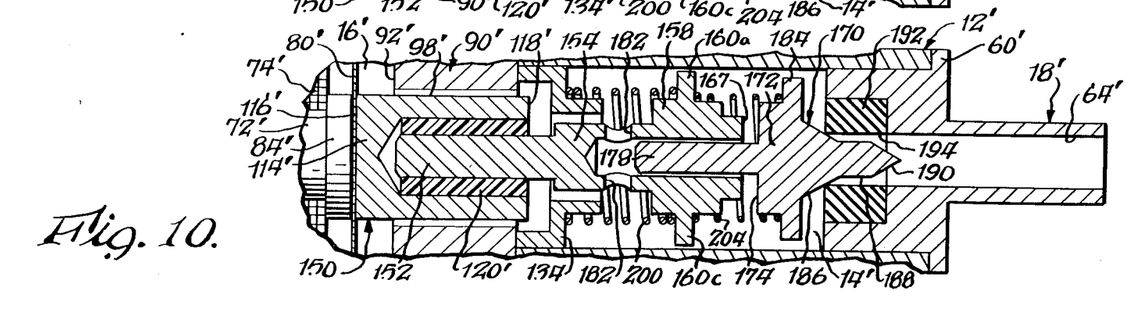
FIG. 10 is a fragmentary longitudinal sectional view of the pump of FIG. 8 showing the armature in an energized position and the check valve in a closed position.
Figure 11:
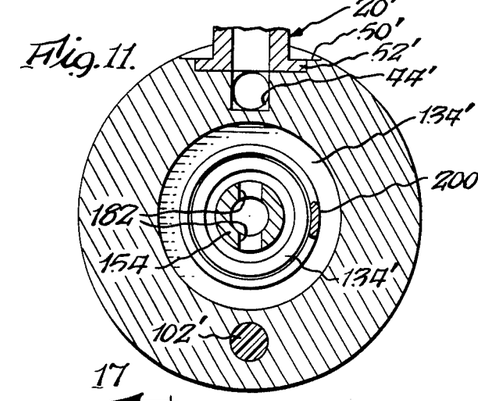
FIG. 11 is a sectional view taken about on line 11—11 in FIG. 8.

When electrical excitation of coil 74' ceases, armature 150 is moved in the opposite direction, i.e. to the right as viewed in FIGS. 8–10, by the force of biasing spring 200 until the armature reaches the rest position as shown in FIG. 9 with surface 186 seated in the opening of passage 194. This motion is relatively slow since it is limited by the small leak rate of fluid between the outer surface of pole portion 114' and the surface passage 98' in body 90' at a pressure difference determined by the force applied by the spring 200. During the return stroke of armature 150 the check valve member 170 is held against the valve seat primarily by the light spring 204 supplemented by the difference between the outlet and inlet pressures acting on the valve seat. Openings 182 allow exit of fluid from the space between passage 168 and valve portion 178. When the return stroke has been completed the spring force is increased to that of spring 200. Thus, the average pumping rate which is determined by the rate or return of armature 150 to the rest position can be relatively slow, but such a pumping rate is called for in typical implantable drug delivery systems. Armature 150 then remains in the rest position of FIG. 9 with inlet 18' closed and waiting for the next forward pumping stroke which occurs when magnet 70' is energized again.

The pump of the embodiment of FIGS. 8–14 has all the advantages of the embodiment of FIGS. 1–7 including the diaphragm 80' providing an hermetic seal between the fluid in housing 12' and the electrical components associated with magnet 70', the immersed armature 150 making operation of the pump nearly independent of ambient pressure, the electric and magnetic efficiency being provided by minimizing the total gap within the magnetic circuit, by having the magnetic pole face 116' of relatively large surface area, and by having core 72' of relatively small diameter, and the pump being relatively small in size and light in weight. In addition, the pump of this embodiment has the further advantage of an integral check valve.

The pump of this embodiment of the present invention is illustrated further by the following example and data. A pump as shown in FIGS. 8–14 was pulsed by a 4.7 microfarad capacitor at 15 volts to pass 0.31 microliters against a 2 p.s.i. head. At a 1 milliliter per day flow rate (3226 pulses per day) the calculated five year energy requirement from the capacitor is 3100 joules. This is approximately 12% of the energy available from a model 7911 lithium-iodine cell commercially available from Wilson Greatbatch Ltd., Clarence, N.Y.

Tables I and II present performance data obtained from operating a pump as shown in FIGS. 8–14 with water, a coil resistance of 243 ohms, a 4.7 microfarad capacitor, and with capacitor charging voltages of 15 volts and 20 volts, respectively:

TABLE I

| Volume Delivered Per Pulse vs. Pressure Increase Capacitor Charging Voltage of 15 Volts | |
|---|---|
| Pressure Increase Across Pump In P.S.I. | Volume Delivered Per Pulse In Microliters |
| 0 | 0.40 |
| 2.0 | 0.31 |
| 3.5 | 0.20 |
| 5.0 | 0.10 |

TABLE II

Volume Delivered Per Pulse vs. Pressure Increase
Capacitor Charging Voltage of 20 Volts

| Pressure Increase Across Pump In P.S.I. | Volume Delivered Per Pulse In Microliters |
|---|---|
| 0 | 0.40 |
| 2.0 | 0.35 |
| 3.5 | 0.25 |
| 5.0 | 0.20 |

Values for volume delivered per pulse and pressure increase across the pump were substantially the same using a capacitor charging voltage of 25 volts.

Tables III and IV present performance data for the pump with water, coil resistance of 243 ohms, 2 p.s.i. pressure difference across the pump, and capacitor magnitudes of 3.3 and 4.7 microfarads, respectively.

TABLE III

Capacitor Energy Per Milliliter vs. Capacitor Voltage
Capacitance of 3.3 Microfarads

| Capacitor Charging Voltage in volts | Energy Per Milliliter Delivered In Joules Per Milliliter |
|---|---|
| 15.0 | 1.3 |
| 20.0 | 2.2 |
| 25.0 | 3.1 |

TABLE IV

Capacitor Energy Per Milliliter vs. Capacitor Voltage
Capacitance of 4.7 Microfarads

| Capacitor Charging Voltage In Volts | Energy Per Milliliter Delivered In Joules Per Milliliter |
|---|---|
| 10.0 | 1.1 |
| 15.0 | 1.7 |
| 20.0 | 2.8 |
| 25.0 | 4.2 |

In the pump from which the foregoing data was obtained, the foward pumping stroke has a duration from about 1 to about 5 milliseconds, depending upon the voltage and the back pressure, and the return stroke has a duration from about 0.1 to about 1.5 seconds.

Figure 15:
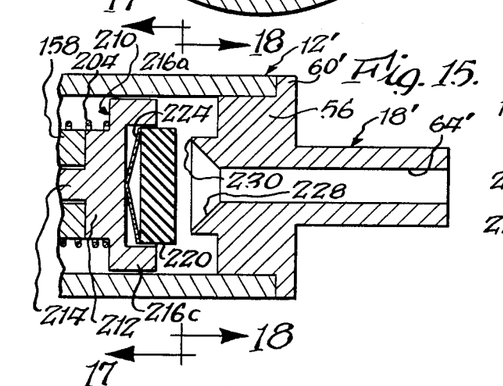
FIG. 15 is a fragmentary longitudinal sectional view showing the pump of FIG. 8 provided with an alternative form of check valve shown in a open position.
Figure 16:
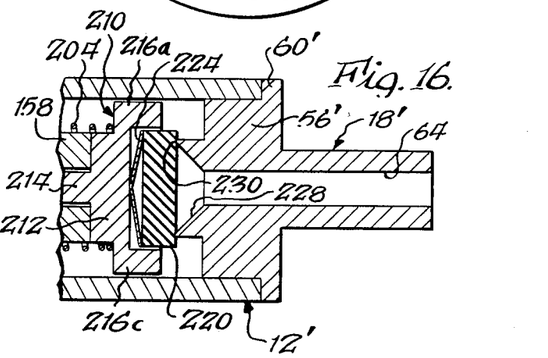
FIG. 16 is a fragmentary longitudinal view similar to FIG. 15 showing the check valve in an closed position.
Figure 17:
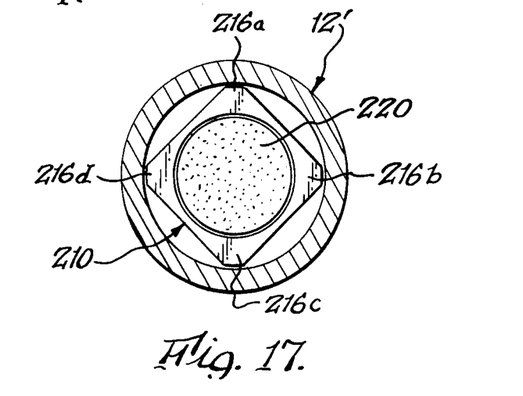
FIG. 17 is a sectional view taken about on line 17—17 in FIG. 15.
Figure 18:
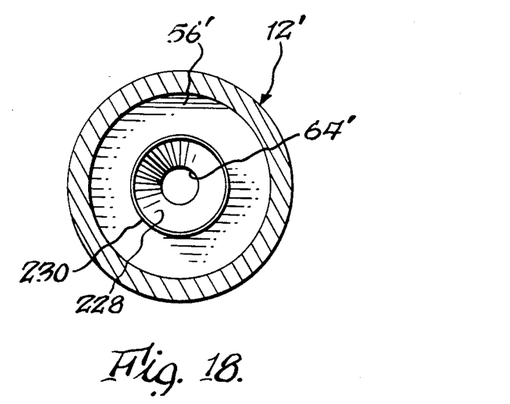
FIG. 18 is a sectional view taken about on line 18—18 in FIG. 15.

FIGS. 15–18 illustrate a modified form of check valve 210 in the pump of FIGS. 8–14. The check valve 210 of FIGS. 15–18 includes a main body portion 212 similar to body 172 of valve member 170 in FIGS. 8–14 and a shaft portion 214 movably received in a longitudinal face of the armature. The body 212 is formed to include a plurality of lands 216a–216d similar to lands 160a–160d which define shoulders for engaging the end of spring 204. The end face of body 212 facing inlet 18' is provided with a recess to accomodate a disc-shaped valve element 220 and a spring-member 224. Disc 220 is of silicon rubber and spring member 224 is a thin disc of titanium foil contoured as shown in FIGS. 15 and 16 to enable disc 220 to rock within the recess. Thus disc 220 is captive within the recess but not attached to it. The passage 64' of the fitting providing inlet 18' terminates in an outwardly flared surface portion 228 defining a valve seat edge 230 of diameter layer than passage 64'. Disc 220 is of slightly larger diameter and is adapted to seat on edge 226. FIGS. 15 and 16 illustrate the unseated and seated conditions of the check valve. The ability of disc 220 to rock within the recess by virtue of spring 224 ensures that disc 220 lies flat on valve seat 230.

The check valve of FIGS. 15–18 has a number of advantages. The flow area in the open portion at the same stroke is relatively larger, and therefore the pressure drop across the check valve is relatively lower. There is no possible leak path around the back of the seat. Seating of valve element 220 on seat 230 does not involve a rubbing motion, and therefore the possibility of unacceptable wear on the seat is reduced. In addition, the arrangement of FIGS. 15–18 is relatively easy to manufacture.

By way of example, in an illustrative pump, valve element 220 has a diameter of about 0.100 inch and a thickness of about 0.030 inch, spring 224 has a diameter of about 0.100 inch and a thickness of about 0.002 inch, and surface 228 defines an angle of about 45° with the housing longitudinal axis.

It is therefore apparent that the present invention accomplishes its intended objective. While several embodiments of the present invention have been described in detail, this is for the purpose of illustration, not limitation.

We claim:
1. An electromagnetic pump comprising:
    (a) an elongated housing having a longitudinal axis and having an interior fluid containing region including a fluid receiving chamber and a fluid pumping chamber in fluid communication therewith, an inlet in fluid communication with said receiving chamber and an outlet in fluid communication with said pumping chamber;
    (b) check valve means operatively associated with said fluid containing region for allowing fluid flow in a direction from said inlet through said outlet and blocking fluid flow in a direction from said outlet through said inlet.
    (c) electromagnet means carried by said housing and located external to said fluid containing region;
    (d) an armature positioned in said fluid containing region of said housing for movement along said housing longitudinal axis and having a pole portion located for magnetic attraction by said electromagnet means and having a plunger portion in said pumping chamber for forcing fluid out of said chamber through said outlet, said armature being movably supported in said housing for movement from a rest position through a forward pumping stroke when attracted by said electromagnet means to force fluid out of said pumping chamber through said outlet and for movement in an opposite direction through a return stroke back to said rest position;
    (e) means for defining a magnetic circuit including said electromagnet means and said armature and a gap between said pole portion of said armature and said electromagnet means for moving said armature toward said electromagnet means to close said gap in response to electrical energization of said electromagnet means;
    (f) said armature pole portion having a pole face disposed in a plane substantially perpendicular to the direction of movement of said armature, said pole face being located to define said gap with said electromagnet means, said pole face being of relatively large area; and
    (g) said fluid containing region of said housing and said electromagnet being in axially spaced relation along said housing longitudinal axis and being separated by barrier means of fluid impervious material disposed substantially perpendicular to said housing longitudinal axis and having axially opposite side, said fluid containing region, inlet, outlet and armature all being located axially on one side of said barrier means and said electromagnet means being located axially on the opposite side of said barrier means.

2. A pump according to claim 1, further including biasing means in said housing for urging said armature toward said rest position.

3. A pump according to claim 1, wherein said armature has a valve portion for closing said inlet when said armature is in said rest position and for opening said inlet when said armature moves through said forward pumping stroke.

4. A pump according to claim 1, further including a body of magnetically permeable material in said housing fluid containing region between said fluid receiving chamber and said fluid pumping chamber, said body defining a portion of said magnetic circuit, said body having a passage therethrough for receiving said armature pole portion in a movable, close-fitting relation whereby said armature moves in said body during said forward and return strokes and said magnetic circuit is through said body and said armature pole portion.

5. A pump according to claim 4, wherein an effective air gap is defined between the inner surface of said passage and the outer surface of said armature pole portion and is introduced in said magnetic circuit, said passage has an axial length, a space having a length is defined between the inner surface of said passage and the outer surface of said armature pole portion, and said passage axial length is relatively large as compared to said length of said space so as to minimize said effective air gap.

6. A pump according to claim 4, wherein each of said body and armature pole portion is provided with an exterior coating of a material which enhances compatibility of fluid being pumped with the exterior surfaces of said body and pole portion.

7. A pump according to claims 4 or 6, wherein said armature pole portion is provided with an exterior coating a fluorpolymer material.

8. A pump according to claim 1, wherein said barrier means comprises a thin plate of metal compatible with the fluid, said electromagnet means includes a housing of magnetically permeable material having an end face contacting one surface of said plate, and further including a body of magnetically permeable material in said housing fluid containing region having a passage through which said armature pole portion moves and having an end face contacting the opposite surface of said plate.

9. A pump according to claim 8, wherein an effective air gap is introduced by said plate in said magnetic circuit and wherein said end faces of said electromagnet housing and said body have areas of contact with said surfaces of said plate which are of sufficient size to minimize said effective gap.

10. A pump according to claim 1, wherein said electromagnet comprises a coil wound on a spool within a housing, said electromagnet housing and said pump housing being located on a common axis, and said spool having a relatively small diameter.

11. A pump according to claim 1, wherein said barrier means is in the form of a thin plate fixed between and providing an hermetic seal between said electromagnet and said fluid-containing region of said housing.

12. A pump according to claim 1, wherein said armature comprises a shaft and an enlarged body on one end of said shaft, said body being of magnetically permeable material and terminating in a pole face disposed substantially perpendicular to the axis of said shaft, the cross-sectional area of said pole face being significantly larger than the cross-sectional area of said shaft, said body and shaft being connected together through a bushing of fluoropolymer material.

13. A pump according to claim 1, wherein said check valve means is operatively coupled to said armature and is located in said fluid-receiving region for opening and closing said inlet.

14. A pump according to claim 1, wherein said check valve means comprises a valve member movably carried by said armature and positioned for closing said inlet when said armature is in said rest position and opening said inlet after said armature begins movement associated with said forward pumping stroke.

15. A pump according to claim 14, further comprising:
(a) first biasing means for urging said armature toward said rest position;
(b) second biasing means for urging said valve member toward a position closing said inlet; and
(c) the force provided by said first biasing means being greater than the force provided by said second biasing means.

16. A pump according to claim 14, wherein said housing is elongated having a longitudinal axis, said armature is elongated having a longitudinal axis disposed substantially parallel to said housing axis, said armature is movable in said housing along said armature longitudinal axis, said inlet is located at one end of said housing, and said check valve member is located on one end of said armature disposed toward said inlet.

17. A pump according to claim 16, wherein said inlet comprises a passage terminating in an annular valve seat facing said valve member and wherein said valve member has a surface moved into and out of contact with said valve seat for closing and opening said inlet.

18. A pump according to claim 17, wherein said valve member surface is provided by a valve element movably carried by said valve member.

19. A pump according to claim 18, further including spring means operatively associated with said valve member and valve element for allowing rocking movement of said valve element relative to said valve member to facilitate seating of said element on said valve seat.

20. A pump according to claim 17, wherein said valve seat has a diameter larger than the diameter of said inlet.

21. A pump according to claim 14, wherein said housing is elongated having a longitudinal axis, said armature is elongated having a longitudinal axis disposed substantially parallel to said housing axis, said armature is movable in said housing along said armature longitudinal axis, said inlet is located at one end of said housing, and said check valve means comprises a valve member movably carried by said armature and located on one end of said armature disposed toward said inlet.

22. A pump according to claim 21, wherein said inlet comprises a passage terminating in an annular valve seat facing said valve member and wherein said valve member has a surface moved into and out of contact with said valve seat for closing and opening said inlet.

23. A pump according to claim 22, wherein said valve member surface is provided by a valve element movably carried by said valve member.

24. A pump according to claim 23, further including spring means operatively associated with said valve member and valve element for allowing rocking movement of said valve element relative to said valve member to facilitate seating of said element on said valve seat.

25. A pump according to claim 22, wherein said valve seat has a diameter larger than the diameter of said inlet.

26. In an electromagnetic pump including a housing having an interior fluid containing region, an inlet and an outlet in fluid communication with said region, electromagnet means carried by said housing and located external to said fluid containing region of said housing, and an armature positioned in said fluid containing region of said housing having a pole portion located for magnetic attraction by said electromagnet means causing movement of said armature to force fluid out of said region through said outlet, the improvement comprising:
   (a) barrier means of fluid-impervious material separating said electromagnet and said fluid containing region of said housing, said barrier means having axially opposite sides and said fluid containing region, inlet, outlet and armature all being located axially on one side of said barrier means and said electromagnet means being located axially on the opposite side of said barrier means;
   (b) a body of magnetically permeable material in said housing fluid containing region and having a passage therethrough for receiving said armature pole portion in a movable, close-fitting relation; and
   (c) means for defining a magnetic circuit including said electromagnet means, said body, the included portions of said barrier means between said electromagnet and said body, said armature pole portion and a gap in said fluid containing region of said housing between said armature pole portion and said electromagnet means for moving said armature toward said electromagnet means to close said gap in response to electrical energization of said electromagnet means.

27. In an electromagnetic pump including a housing having a longitudinal axis and having an interior fluid containing region, an inlet and an outlet in fluid communication with said region, electromagnet means carried by said housing and located external to said fluid-containing region, and an armature positioned in said housing for movement along said housing longitudinal axis from a rest position through a forward pumping stroke when attracted by said electromagnet means to force fluid out of said fluid containing region through said outlet and for movement in an opposite direction through a return stroke back to said rest position, said fluid containing region of said housing and said electromagnet means being in axially spaced relation along said housing longitudinal axis, the improvement comprising:
   (a) check valve means operatively carried by said armature and located in said fluid containing region of said housing adjacent said inlet for closing said inlet when said armature is in said rest position and for opening said inlet after said armature begins movement associated with said forward pumping stroke, said check valve means allowing fluid flow in a direction from said inlet through said outlet and blocking fluid flow in a direction from said outlet through said inlet; and
   (b) barrier means of fluid-impervious material separating said electromagnet and said fluid containing region of said housing, said barrier means having axially opposite sides and said fluid containing region, inlet, outlet and armature all being located axially on one side of said barrier means and said electromagnet means being located axially on the opposite side of said barrier means.

28. An improved electromagnetic pump according to claim 27, wherein said check valve means comprises a valve member movably carried by said armature, and further including:
   (a) first biasing means for urging said armature toward said rest position;
   (b) second biasing means for urging said valve member toward a position closing said inlet; and
   (c) the force provided by said first biasing means being greater than the force provided by said second biasing means.

29. An electromagnetic pump comprising:
   (a) a housing having an interior fluid containing region including a fluid receiving chamber and a fluid pumping chamber in fluid communication therewith, an inlet in fluid communication with said receiving chamber and an outlet in fluid communication with said pumping chamber;
   (b) check valve means operatively associated with said fluid containing region for allowing fluid flow in a direction from said inlet through said outlet and blocking fluid flow in a direction from said outlet through said inlet;
   (c) electromagnet means carried by said housing and located external to said fluid containing region;
   (d) said fluid-containing region of said housing and said electromagnet being separated by barrier means of fluid impervious material;
   (e) an armature positioned in said fluid containing region of said housing having a pole portion located for magnetic attraction by said electromagnet means and having a plunger portion in said pumping chamber for forcing fluid out of said chamber through said outlet; said armature being movably supported in said housing for movement from a rest position through a forward pumping stroke when attracted by said electromagnet means to force fluid out of said pumping chamber through said outlet and for movement in an opposite direction through a return stroke back to said rest position;
   (f) barrier means of fluid-impervious material separating said electromagnet and said fluid containing region of said housing, said barrier means having axially opposite sides and said fluid containing region, inlet, outlet and armature all being located axially on one side of said barrier means and said electromagnet means being located axially on the opposite side of said barrier means;
   (g) means for defining a magnetic circuit including said electromagnet means and said armature and a gap between said pole portion of said armature and said electromagnet means for moving said armature toward said electromagnet means to close said gap in response to electrical energization of said electromagnet means; and
   (h) a body of magnetically permeable material in said housing fluid containing region between said fluid receiving chamber and said fluid pumping chamber, said body defining a portion of said magnetic circuit, said body having a passage therethrough for receiving said armature pole portion in a movable, close-fitting relation whereby said armature moves in said body during said forward and return strokes and said magnetic circuit is through said body and said armature pole portion.

30. An electromagnetic pump comprising:
(a) an elongated housing having a longitudinal axis and having an interior fluid containing region including a fluid receiving chamber and a fluid pumping chamber in fluid communication therewith, an inlet in fluid communication with said receiving chamber and an outlet in fluid communication with said pumping chamber;
(b) check valve means operatively associated with said fluid containing region for allowing fluid flow in a direction from said inlet through said outlet and blocking fluid flow in a direction from said outlet through said inlet;
(c) electromagnet means carried by said housing and located external to said fluid containing region;
(d) an armature positioned in said fluid containing region of said housing for movement along said housing longitudinal axis and having a pole portion located for magnetic attraction by said electromagnet means and having a plunger portion in said pumping chamber for forcing fluid out of said chamber through said outlet, said armature being movably supported in said housing for movement from a rest position through a forward pumping stroke when attracted by said electromagnet means to force fluid out of said pumping chamber through said outlet and for movement in an opposite direction through a return stroke back to said rest position;
(e) means for defining a magnetic circuit including said electromagnet means and said armature and a gap between said pole portion of said armature and said electromagnet means for moving said armature toward said electromagnet means to close said gap in response to electrical energization of said electromagnet means;
(f) said armature pole portion having a pole face disposed in a plane substantially perpendicular to the direction of movement of said armature, said pole face being located to define said gap with said electromagnet means, said pole face being of relatively large area;
(g) said fluid containing region of said housing and said electromagnet means being in axially spaced relation along said housing longitudinal axis and being separated by barrier means of fluid impervious material;
(h) a body of magnetically permeable material in said housing fluid containing region between said fluid receiving chamber and said fluid pumping chamber, said body defining a portion of said magnetic circuit, said body having a passage therethrough for receiving said armature pole portion in a movable, close-fitting relation whereby said armature moves in said body during said forward and return strokes and said magnetic circuit is through said body and said armature pole portion; and
(i) said passage in said body having a cross-sectional size and said armature pole portion having a cross-sectional dimension, said size and said dimension being so related to define a leakage path for fluid from said pumping chamber to said receiving chamber during movement of said armature through said return stroke.

31. An electromagnetic pump comprising:
(a) an elongated housing having a longitudinal axis and having an interior fluid containing region including a fluid receiving chamber and a fluid pumping chamber in fluid communication therewith, an inlet in fluid communication with said receiving chamber and an outlet in fluid communication with said pumping chamber;
(b) check valve means operatively associated with said fluid containing region for allowing fluid flow in a direction from said inlet through said outlet and blocking fluid flow in a direction from said outlet through said inlet;
(c) electromagnet means carried by said housing and located external to said fluid containing region;
(d) an armature positioned in said fluid containing region of said housing for movement along said housing longitudinal axis and having a pole portion located for magnetic attraction by said electromagnet means and having a plunger portion in said pumping chamber for forcing fluid out of said chamber through said outlet, said armature being movably supported in said housing for movement from a rest position through a forward pumping stroke when attracted by said electromagnet means to force fluid out of said pumping chamber through said outlet and for movement in an opposite direction through a return stroke back to said rest position;
(e) means for defining a magnetic circuit including said electromagnet means and said armature and a gap between said pole portion of said armature and said electromagnet means for moving said armature toward said electromagnet means to close said gap in response to electrical energization of said electromagnet means;
(f) said armature pole portion having a pole face disposed in a plane substantially perpendicular to the direction of movement of said armature, said pole face being located to define said gap with said electromagnet means, said pole face being of relatively large area;
(g) said fluid containing region of said housing and said electromagnet being in axially spaced relation along said housing longitudinal axis;
(h) barrier means of fluid-impervious material separating said electromagnet and said fluid-containing region of said housing, said barrier means comprising a thin plate of metal compatible with the fluid, fixed between and providing hermetic seal between said electromagnet and said fluid containing region of said housing; and
(i) a body of magnetically permeable material in said housing fluid containing region between said fluid receiving chamber and said fluid pumping chamber, said body having a passage therethrough for receiving said armature pole portion in a movable, close-fitting relation whereby said armature moves in said body during said forward and return strokes, said armature pole portion co-operating with said passage to define a leakage path for fluid from said pumping chamber to said receiving chamber during movement of said armature through said return stroke;
(j) whereby said magnetic circuit includes said body, said armature pole portion and the portions of said barrier plate associated with said electromagnet.

32. A pump according to claim 31, wherein pumping chamber is defined between said barrier plate and said body, said armature pole portion moves in said pumping chamber and has a pole face on the end thereof disposed toward said barrier plate, and said gap is defined between said armature pole face and said barrier plate, whereby as said gap is reduced during energization of said electromagnet causing the forward pumping stroke the movement of said armature pole face toward said barrier plate forces fluid out of said pumping chamber through said housing outlet.

33. A pump according to claim 31, wherein said electromagnet means includes a housing of magnetically permeable material having an end face contacting one surface of said barrier plate, said body has an end face contacting the other surface of said plate, an effective air gap is introduced by said plate in said magnetic circuit, and end faces of said electromagnet housing and said body have areas of contact with said surface of said plate which are of sufficient size to minimize said effective air gap.

34. A pump according to claim 31, wherein an effective air gap is defined between the inner surface of said passage and the outer surface of said armature pole portion and is introduced in said magnetic circuit, said passage has an axial length, a space having a length is defined between the inner surface of said passage and the outer surface of said armature pole portion, and said passage axial length is relatively large as compared to said length of said space so as to minimize said effective air gap.

35. In an electromagnetic pump including a housing having an interior fluid containing region, and inlet and an outlet in fluid communication with said region, electromagnet means carried by said housing and located external to said fluid containing region of said housing, and an armature positioned in said fluid containing region of said housing having a pole portion located for magnetic attraction by said electromagnet means causing movement of said armature to force fluid out of said region through said outlet, the improvement comprising:
   (a) barrier means of fluid-impervious material separating said electromagnet and said fluid containing region of said housing;
   (b) a body of magnetically permeable material in said housing fluid containing region and having a passage therethrough for receiving said armature pole portion in a movable, close-fitting relation;
   (c) means for defining a magnetic circuit including said electromagnet means, said body, the included portions of said barrier means between said electromagnet and said body, said armature pole portion and a gap in said fluid containing region of said housing between said armature pole portion and said electromagnet means for moving said armature toward said electromagnet means to close said gap in response to electrical energization of said electromagnet means; and
   (d) said barrier means comprising a thin metal plate fixed between and providing an hermetic seal between said electromagnet and said fluid containing region of said housing, said electromagnet means including a housing of magnetically permeable material having an end face contacting one surface of said barrier plate, said body having an end face contacting the other surface of said plate, and the areas of contact of said end faces of said electromagnet housing and said body with said surface of said plate being of sufficient size to to minimize the effective air gap introduced by said plate in said magnetic circuit.

36. A pump according to claim 35, wherein the axial length of said passage in said body is relatively long as compared to the length of the space between the inner surface of said passage and the outer surface of said armature pole portion to minimize the effective air gap defined therebetween introduced in said magnetic circuit.

37. An electromagnetic pump comprising:
   (a) a housing having an interior fluid containing region including a fluid receiving chamber and a fluid pumping chamber in fluid communication therewith, an inlet in fluid communication with said receiving chamber and an outlet in fluid communication with said pumping chamber;
   (b) check valve means operatively associated with said fluid containing region for allowing fluid flow in a direction from said outlet through said inlet;
   (c) electromagnet means carried by said housing and located external to said fluid containing region;
   (d) said fluid-containing region of said housing and said electromagnet being separated by barrier means of fluid impervious material;
   (e) an armature positioned in said fluid containing region of said housing having a pole portion located for magnetic attraction by said electromagnet means and having a plunger portion in said pumping chamber for forcing fluid out of said chamber through said outlet; said armature being movably supported in said housing for movement from a rest position through a forward pumping stroke when attracted by said electromagnet means to force fluid out of said pumping chamber through said outlet and for movement in an opposite direction through a return stroke back to said rest position;
   (f) means for defining a magnetic circuit including said electromagnet means and said armature and a gap between said pole portion of said armature and said electromagnet means for moving said armature toward said electromagnet means to close said gap in response to electrical energization of said electromagnet means;
   (g) a body of magnetically permeable material in said housing fluid containing region between said fluid receiving chamber and said fluid pumping chamber, said body defining a portion of said magnetic circuit, said body having a passage therethrough for receiving said armature pole portion in a movable, close-fitting relation whereby said armature moves in said body during said forward and return strokes and said magnetic circuit is through said body and said armature pole portion; and
   (h) said passage in said body having a cross-sectional size and said armature pole portion having a cross-sectional dimension, said size and said dimension being so related to define a leakage path for fluid from said pumping chamber to said receiving chamber during movement of said armature through said return stroke.

38. A pump according to claim 37, wherein an effective air gap is defined between the inner surface of said passage and the outer surface of said armature pole portion and is introduced in said magnetic circuit, said passage has an axial length, a space having a length is defined between the inner surface of said passage and the outer surface of said armature pole portion, and said passage axial length is relatively large as compared to said length of said space so as to minimize said effective air gap.

39. A pump according to claim 37, wherein said armature pole portion has a pole face disposed in a plane substantially perpendicular to the direction of movement of said armature, said pole face being located to define said gap with said electromagnet means, said pole face being of relatively large area.

40. An electromagnetic pump comprising:
(a) a housing having an interior fluid containing region including a fluid receiving chamber and a fluid pumping chamber in fluid communication therewith, an inlet in fluid communication with said receiving chamber and an outlet in fluid communication with said pumping chamber;
(b) check valve means operatively associated with said fluid containing region for allowing fluid flow in a direction from said inlet through said outlet and blocking fluid flow in a direction from said outlet through said inlet;
(c) electromagnet means carried by said housing and located external to said fluid containing region;
(d) said fluid-containing region of said housing and said electromagnet being separated by barrier means of fluid impervious material;
(e) an armature positioned in said fluid containing region of said housing having a pole portion located for magnetic attraction by said electromagnet means and having a plunger portion in said pumping chamber for forcing fluid out of said chamber through said outlet; said armature being movably supported in said housing for movement from a rest position through a forward pumping stroke when attracted by said electromagnet means to force fluid out of said pumping chamber through said outlet and for movement in an opposite direction through a return stroke back to said rest position;
(f) means for defining a magnetic circuit including said electromagnet means and said armature and a gap between said pole portion of said armature and said electromagnet means for moving said armature toward said electromagnet means to close said gap in response to electrical energization of said electromagnet means;
(g) a body of magnetically permeable material in said housing fluid containing region between said fluid receiving chamber and said fluid pumping chamber, said body defining a portion of said magnetic circuit, said body having a passage therethrough for receiving said armature pole portion in a movable, close-fitting relation whereby said armature moves in said body during said forward and return strokes and said magnetic circuit is through said body and said armature pole portion; and
(h) said barrier means comprising a thin plate of metal compatible with the fluid, said electromagnet means including a housing of magnetically permeable material having an end face contacting one surface of said plate, and said body of magnetically permeable material in said housing fluid containing region has an end face contacting the opposite surface of said plate.

41. A pump according to claim 40; wherein an effective air gap is introduced by said plate in said magnetic circuit and wherein said end faces of said electromagnet housing and said body have areas of contact with said surfaces of said plate which are of sufficient size to minimize said effective gap.

42. An electromagnetic pump comprising:
(a) a housing having an interior fluid containing region including a fluid receiving chamber and a fluid pumping chamber in fluid communication therewith, an inlet in fluid communication with said receiving chamber and an outlet in fluid communication with said pumping chamber;
(b) check valve means operatively associated with said fluid containing region for allowing fluid flow in a direction from said inlet through said outlet and blocking fluid flow in a direction from said outlet through said inlet;
(c) electromagnet means carried by said housing and located external to said fluid containing region;
(d) said fluid-containing region of said housing and said electromagnet being in side-by-side relation and separated by barrier means of fluid impervious material;
(e) an armature positioned in said fluid containing region of said housing having a pole portion located for magnetic attraction by said electromagnet means and having a plunger portion in said pumping chamber for forcing fluid out of said chamber through said outlet; said armature being movably supported in said housing for movement from a rest position through a forward pumping stroke when attracted by said electromagnet means to force fluid out of said pumping chamber through said outlet and for movement in an opposite direction through a return stroke back to said rest position;
(f) means for defining a magnetic circuit including said electromagnet means and said armature and a gap between said pole portion of said armature and said electromagnet means for moving said armature toward said electromagnet means to close said gap in response to electrical energization of said electromagnet means;
(g) a body of magnetically permeable material in said housing fluid containing region between said fluid receiving chamber and said fluid pumping chamber, said body defining a portion of said magnetic circuit, said body having a passage therethrough for receiving said armature pole portion in movable relation whereby said armature moves in said body during said forward and return strokes and said magnetic circuit is through said body and said armature pole portion; and
(h) said barrier means having opposite sides, said fluid containing region, inlet, outlet and armature all being located axially on one side of said barrier means and said electromagnet means being located on the opposite side of said barrier means.

* * * * *